United States Patent [19]

DeVries

[11] Patent Number: 4,967,762

[45] Date of Patent: Nov. 6, 1990

[54] BIOPSY SYRINGE WITH SUCTION VENT

[75] Inventor: James H. DeVries, Grand Rapids, Mich.

[73] Assignee: DLP, Inc., Grand Rapids, Mich.

[21] Appl. No.: 347,717

[22] Filed: May 5, 1989

[51] Int. Cl.$^5$ ............................................. A61B 10/00
[52] U.S. Cl. ...................................... 128/753; 128/766; 604/236
[58] Field of Search ............... 128/749, 752, 753, 763, 128/765–766, 770; 604/187, 236–238, 240, 256

[56] References Cited

U.S. PATENT DOCUMENTS

| | | | |
|---|---|---|---|
| 3,957,052 | 5/1976 | Topham | 604/236 |
| 4,549,554 | 10/1985 | Markham | 128/753 |
| 4,844,087 | 7/1989 | Gary | 128/753 |

FOREIGN PATENT DOCUMENTS

| | | | |
|---|---|---|---|
| 87197 | 5/1966 | France | 128/763 |
| 2609624 | 7/1988 | France | 128/749 |

*Primary Examiner*—Max Hindenburg
*Attorney, Agent, or Firm*—Barnes, Kisselle, Raisch, Choate, Whittemore & Hulbert

[57] ABSTRACT

A needle hub for use with a syringe in obtaining biopsy specimens. A needle is inserted into the area from which a specimen is to be taken. A vacuum is pulled on the needle lumen to cause tissue to be drawn into the lumen. A special vacuum release is provided on the needle hub so that a surgeon can roll back an O-ring in the hub to expose the interior of the hub to atmosphere, thus releasing the vacuum pull on the needle lumen and allowing the needle to be withdrawn without dilution of the specimen, or contamination by material from other sites.

2 Claims, 1 Drawing Sheet

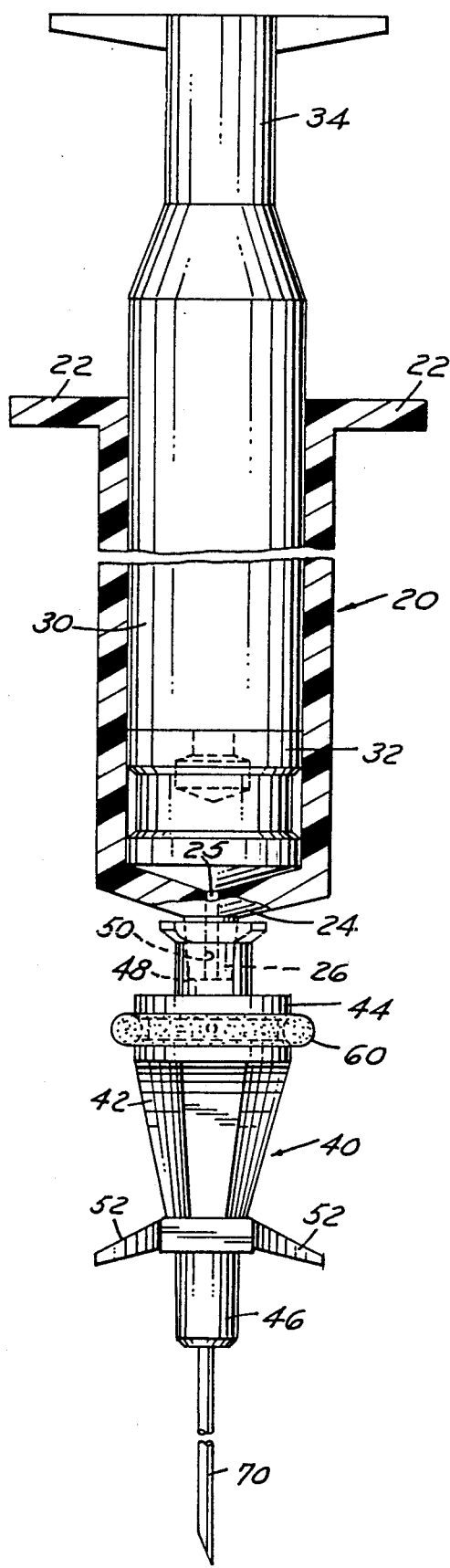
FIG.1
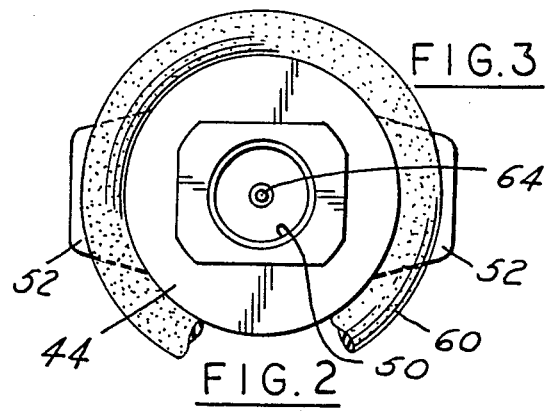
FIG.3 FIG.2
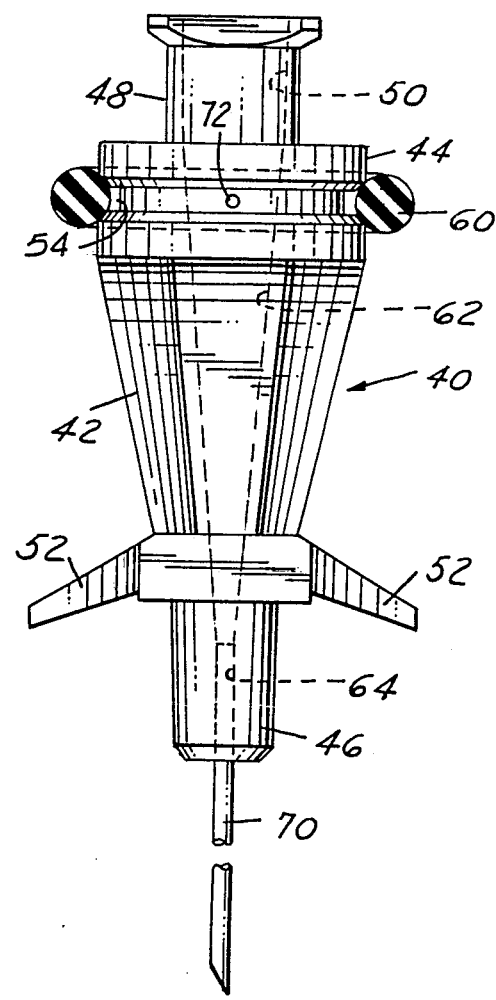
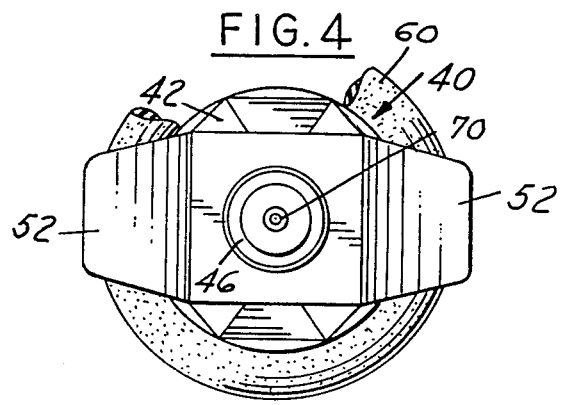
FIG.4

BIOPSY SYRINGE WITH SUCTION VENT

FIELD OF INVENTION

Syringe and needle combination used for percutaneous procedures in connection with diagnostic, biopsy, guidewire insertion, and other vessel intrusive treatment.

BACKGROUND AND FEATURES OF THE INVENTION

A syringe used in medical procedures usually consists of an outer chamber of cylindrical shape containing a plunger or piston movable in the chamber by manual manipulation of an actuator which projects from the piston to the exterior of the chamber. The chamber of the syringe ends in a body portion called a hub which carries a hollow needle called a cannula having an interior passage called a lumen. The needles usually have a sharpened point to facilitate the percutaneous insertion. These syringes may be used to draw in a liquid medication by withdrawal of the piston in the chamber and inject the medication intravenously into a vein by moving the piston into the chamber. Inversely, the syringe may be used to insert into a blood vessel for the purpose of withdrawing blood samples for diagnostic test purposes.

The syringe also has a function in biopsy procedures. Most biopsy procedures are accomplished by inserting a hollow tube (cannula) into an area to be tested. The targeted tissue moves into a side recess in the cannula and a second knife-like sleeve moves over the recess to incise the tissue and trap it in the cannula so it can be removed for inspection by a pathologist.

Within the last decade, a new biopsy procedure has been receiving acceptance. It is referred to as the "skinny" needle technique and is particularly useful in obtaining biopsy samples deep within the body. If an X-ray or mammogram shows an area which appears to be suspect, the "skinny" needle in the form of a very thin tube, perhaps seven-tenths of a millimeter in diameter, can be inserted into the area to be checked. This technique can be used for checking areas within a breast, in the lung, in the pancreas, in the liver, in the prostate, in the thyroid, in lymph nodes and other area deep within the body. The insertion causes minimal trauma to the patient and is generally done in cooperation with an X-ray technician (radiologist) who assists in the directing of the end of the thin needle to the area targeted. Measurements made from X-rays or pictures obtained by ultrasound determine the angle of the thrust and the depth of penetration of the needle.

The present invention is especially pertinent to this fine needle technique since once the needle has reached the sensitive area, a vacuum is drawn on the inner passage of the needle to draw in cells to be studied under a microscope. Thus, the fine needle is attached to the hub of the syringe and guided into the patient. A withdrawal of the syringe plunger draws the cells into the end of the needle which is then withdrawn from the patient. A problem exists when the applied suction continues aspirating unwanted cells or fluids as the needle is withdrawn. It is not practical to push in the plunger for fear of discharging the vital tissue sample. The present invention is directed to a means of relieving the negative pressure (suction) in a manner which is controlled by the operator and requires only a quick and simple finger manipulation at the syringe.

The object of the invention is accomplished by an attachment to a syringe hub of a secondary hub carrying the needle. An annular device such as an O-ring is mounted on an annular groove in the secondary hub and this groove has a port in communication with the interior of the hub. Normally, this ring seals the port but a slight rolling of the ring opens the port to atmosphere and relieves the negative pressure. Then the needle can be withdrawn safely carrying the desired specimen in the end.

Other objects and features of the invention will be apparent in the following description and claims in which the principles of the invention are set forth together with details to enable persons skilled in the art to practice the invention, all in connection with the best mode presently contemplated for the invention.

BRIEF DESCRIPTION OF THE DRAWINGS

DRAWINGS accompany the disclosure and the various views thereof may be briefly described as:

FIG. 1, a sectional view of a combined syringe and needle hub.

FIG. 2, an enlarged view of the needle hub.

FIG. 3, a proximal end view of the needle hub.

FIG. 4, a distal end view of the needle hub.

DETAILED DESCRIPTION OF THE INVENTION AND THE MANNER AND PROCESS OF USING IT

With reference to the drawings, in FIG. 1, a syringe cylinder 20 has finger extensions 22 and a hub end 24 with a central opening 25 which, under normal use, will carry a needle appropriate to the intended use. The hub has a tapered projection 26. Within the cylinder 20 is a plunger 30 with a resilient piston seal attachment 32 which has a relatively tight but sliding fit with the inner wall of the cylinder. The plunger 30 extends out of the cylinder to a manipulatable end 34 to facilitate movement in and out.

At the lower end of the syringe is a needle hub attachment 40 having a body portion 42 tapering from a proximal end 44 to a hub end 46. A connector neck 48 at the proximal end has a tapered recess 50 to receive projection 26 on the syringe body in a tight friction fit. Finger wings 52 facilitate the assembly and manipulation of the combined hub 40 and the syringe 20.

At the top end 44 of needle hub 40 is an annular groove 54 (FIG. 2) which carries an O-ring 60. The interior of the needle hub 40 has a tapered central passage 62, the top end of which receives the hub projection 26 of the syringe and the smaller end terminating at a central opening 64 which receives and carries a needle 70. Between the internal passage 62 and the annular groove 54 is a radial port 72 which provides communication between the passage 62 and the groove 54. This port 72 is normally blocked by the O-ring 60 located in the groove 54. It will be seen that when the pliable O-ring 60 is rolled out of the groove 54 at any point around the circumference, the interior passage 62 of the hub 40 and also the interior of the syringe below the piston 32 is open to atmosphere. Thus, any vacuum (pressure below atmospheric) will be restored to atmospheric pressure.

It will be appreciated that the syringe body 20 could be constructed to include the needle hub as an integral part to provide the special pressure relief system described. Using the independent needle hub makes it possible to have this suction release unit used with any standard syringe.

As indicated in the introduction, the needle 70 can be of the fine needle variety (skinny needle) with diameters below a millimeter and a lumen even smaller. With the help of a skilled radiologist, the end of the needle can be located in the area of tissue sought to be tested. A suction is then pulled on the syringe by pulling back the piston 32 to introduce a small specimen of tissue into the needle lumen. Once this is accomplished, the surgeon rolls the O-ring to expose the port 72 and the suction is released. The needle can then be withdrawn and the specimen examined by a pathologist.

What is claimed is:

1. A syringe assembly for use in biopsy procedures which comprises:
   (a) a syringe cylinder having a needle hub with an axial passage,
   (b) a piston in said cylinder movable to produce pressure or vacuum in said hub passage,
   (c) first means on said hub to receive and retain a biopsy needle having a lumen in communication with said passage and projectible into an area to be pathologically explored,
   (d) second means on said first means independent of said piston to admit atmospheric pressure to said needle lumen to relieve the suction in said lumen, and
   (e) said second means comprising means forming a port on said first means in communication with said axial passage, and movable means to close said port and shiftable to open said port to atmosphere, said first means having an annular external groove, and said port extending from said groove to said axial passage, and said movable means comprising a flexible O-ring in said groove positioned to close said port and movable manually away from groove to open said port to atmosphere.

2. A syringe assembly for use in biopsy procedures which comprises:
   (a) a syringe cylinder having a needle hub with an axial passage,
   (b) a piston in said cylinder movable to produce pressure or vacuum in said hub passage,
   (c) first means on said hub to receive and retain a biopsy needle having a lumen in communication with said passage and projectible into an area to be pathologically explored,
   (d) second means on said first means independent of said piston to admit atmospheric pressure to said needle lumen to relieve the suction in said lumen, and
   (e) said first means on said hub comprising a body having a central passage engaged at one proximal end with said syringe hub, and retaining a biopsy needle at the distal end, and said second means comprising movable valve means having an open and closed position on said body to connect a radial port in said body to said central passage when shifted to open position,
   (f) said body having an annular outer groove in communication with said port, and an O-ring in said groove in one position to close said port and movable to a second position to open said port.

* * * * *